United States Patent [19]

Boigegrain et al.

[11] Patent Number: 4,515,951
[45] Date of Patent: May 7, 1985

[54] PREPARATION OF 5,6,7,7A-TETRAHYDRO-4H-THIENO[3,2-C]PYRIDIN-2-ONE COMPOUNDS

[75] Inventors: Robert Boigegrain; Jean-Pierre Maffrand, both of Portet-sur-Garonne, France; Norio Suzuki, Chiba, Japan; Kynichi Matsubayachi, Funabashi, Japan; Shinichiro Ashida, Ichikawa, Japan

[73] Assignee: Sanofi, Paris, France

[21] Appl. No.: 635,461

[22] Filed: Jul. 25, 1984

Related U.S. Application Data

[62] Division of Ser. No. 325,805, Nov. 30, 1981, abandoned.

[30] Foreign Application Priority Data

Nov. 28, 1980 [FR] France .................. 80 25274

[51] Int. Cl.³ .......................................... C07D 495/04
[52] U.S. Cl. ............................................. 546/114
[58] Field of Search .......................... 546/114; 549/52

[56] References Cited

U.S. PATENT DOCUMENTS

4,097,482 6/1978 Amselem .............................. 546/114
4,424,356 1/1984 Maffrand et al. ...................... 546/114
4,458,074 7/1984 Bouscuet et al. ...................... 546/114

OTHER PUBLICATIONS

Elguero et al., *The Tautomerism of Heterocycles,* Supplement 1, (1976), p. 229.

*Primary Examiner*—Robert W. Ramsuer
*Attorney, Agent, or Firm*—Weiser & Stapler

[57] ABSTRACT

The present invention provides derivatives of 5,6,7,7a-tetrahydro-4H-thieno[3,2-c]pyridin-2-one of the general formula:

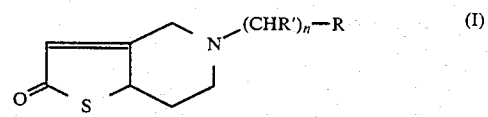

in which R is a hydrogen atom or a phenyl radical, which is optionally substituted by at least one halogen atom or lower alkyl radical, lower alkoxy radical, nitro group, carboxyl group, alkoxycarbonyl radical or cyano group, R' is a hydrogen atom or a lower alkyl radical and n is 0, 1, 2, 3, or 4; and the addition salts thereof with pharmaceutically acceptable mineral or organic acids.

The present invention also provides a process for the preparation of these compounds, as well as pharmaceutical compositions containing them.

13 Claims, No Drawings

PREPARATION OF 5,6,7,7A-TETRAHYDRO-4H-THIENO[3,2-C]PYRIDIN-2-ONE COMPOUNDS

This application is a division, of application Ser. No. 325,805, filed Nov. 30, 1981.

The present invention is concerned with derivatives of 5,6,7,7a-tetrahydro-4H-thieno[3,2-c]pyridin-2-ones, with the preparation thereof and with the use thereof in human and veterinary medicine.

The compounds according to the present invention have the general formula:

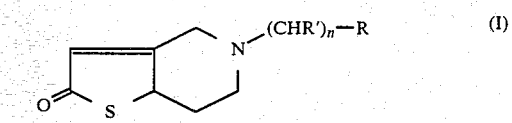

in which R is a hydrogen atom or a phenyl radical, which is optionally substituted by at least one halogen atom or lower alkyl radical, lower alkoxy radical, nitro group, carboxyl group, alkoxycarbonyl radical or cyano group; R' is a hydrogen atom or a lower alkyl radical and n is 0, 1, 2, 3 or 4; and the addition salts thereof with pharmaceutically acceptable mineral and organic acids.

In a preferred group of compounds according to the present invention, R is a phenyl radical, which is optionally substituted by a halogen atom, a $C_1$-$C_4$ alkyl radical, a nitro group or a cyano group, R' is a hydrogen atom or a $C_1$-$C_4$ alkyl radical and n is 1.

These compounds, which contain at least one asymmetrical carbon atom, can exist in the form of several stereoisomers (enantiomers or diastereoisomers). The present invention is also concerned with these stereoisomers and mixtures thereof.

These compounds, which have anti-platelet aggregation and anti-thrombosis properties, are covered by a general formula, given in French Patent Specification Nos. 73 03 503 and 75 24 486, in the following tautomeric form:

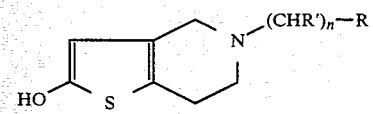

in which R, R' and n have the same meanings as above.

However, none of the compounds according to the present invention is specifically described therein.

Furthermore, the toxicological and pharmacological study of the compounds of the present invention has revealed special properties both in respect of efficacy and tolerance and in respect of the actual nature of these properties.

The present invention also provides a process for the preparation of the compounds of general formula (I), wherein:

(a) a boronic acid derivative of the general formula:

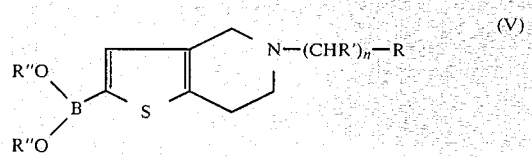

in which R, R' and n have the same meanings as above and R" is a hydrogen atom or a lower alkyl radical, is oxidised, and (b) the boric acid derivative obtained of the general formula:

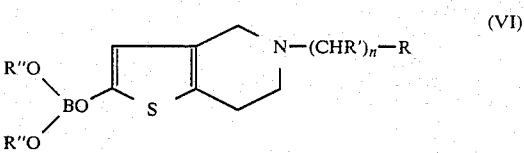

in which R, R', R" and n have the same meanings as above, is hydrolysed to give a compound of general formula (I).

The oxidation of the boronic acid derivative (V), which can be a boronate (Va) or a boronic acid (Vb), is carried out in an inert solvent under conditions which prevent a rise in temperature of the reaction mixture.

The preparation of the boronic acid derivative of general formula (V) can be carried out in accordance with the two variants described below, depending upon whether the compound is a boronate (Va) or a boronic acid (Vb), these two variants having a common preliminary starting point.

At the common starting point, a compound of general formula (II), in which X is the —$(CHR')_n$R radical defined above or is the trimethylsilyl radical, is reacted with an alkyl-lithium compound, such as butyllithium, or a lithium amide, such as lithium diisopropylamide, to give a lithium derivative (III) which is condensed in the same reaction vessel with an alkyl borate of the general formula $B(OR''')_3$, in which R''' is a lower alkyl radical, such as tri-n-butyl borate, to give a boronate of general formula (IV), in accordance with the following reaction scheme:

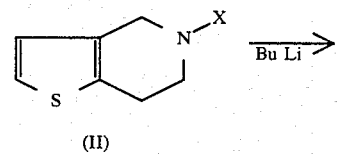

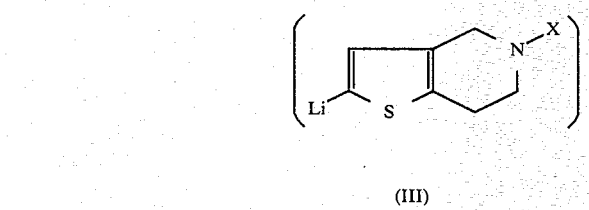

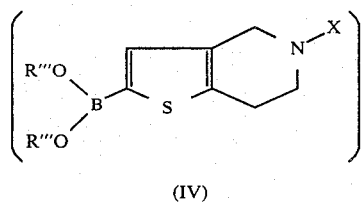

(IV)

The formation of the lithium derivative takes place in an inert solvent, such as diethyl ether, tetrahydrofuran or hexane, optionally in the presence of a complexing agent, such as hexamethylphosphotriamide, at a temperature of from −50° to +30° C.

The borate is added at a temperature of from 0° to −80° C. and the temperature is then allowed to rise again, where appropriate, to ambient temperature.

According to a first variant, in which X is a —(CHR')$_n$—R radical, the boronate of general formula (Va), in which R'' is a lower alkyl radical, is treated in the same reaction vessel with 30% aqueous hydrogen peroxide. This gives a borate of general formula (VIa), the immediate hydrolysis of which in the reaction mixture gives a compound of general formula (I), in accordance with the following reaction scheme:

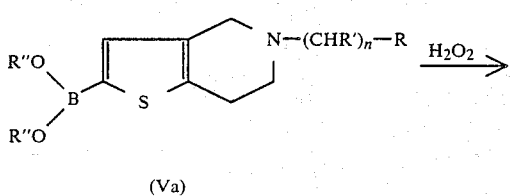

(Va)

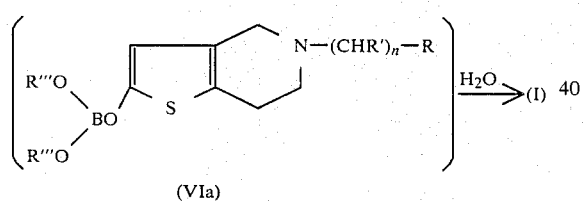

(VIa)

According to a second variant, carried out at the end of the common sequence, a boronate of general formula (IV), in which X is a trimethylsilyl radical, is treated with 3N hydrochloric acid in accordance with the following reaction scheme:

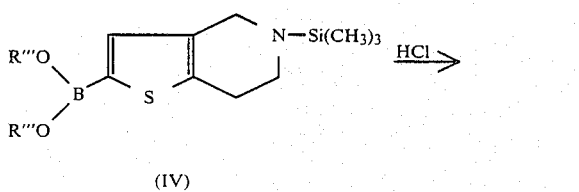

(IV)

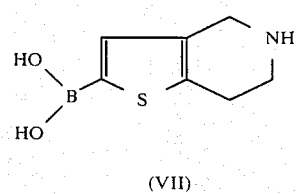

(VII)

The resulting boronic acid of general formula (VII) is then alkylated with a compound of the general formula R(CHR')$_n$—Y, in which R, R' and n have the same meanings as above and Y is a halogen atom, preferably a chlorine, bromine or iodine atom, or an arylsulphonyloxy radical, such as a p-toluenesulphonyloxy or benzenesulphonyloxy radical, or an alkylsulphonyloxy radical, such as a methanesulphonyloxy radical, to give a hygroscopic derivative which is a boronic acid of general formula (Vb). It is not necessary to purify this compound before converting it, in accordance with the same reaction procedure as employed for the boronate of general formula (Va) in the preceding variant, into a boric acid derivative of general formula (VIb), and then into a compound of general formula (I), by first treating (Vb) with an aqueous hydrogen peroxide solution and then carrying out an aqueous hydrolysis of (VIb). The reaction scheme is shown below:

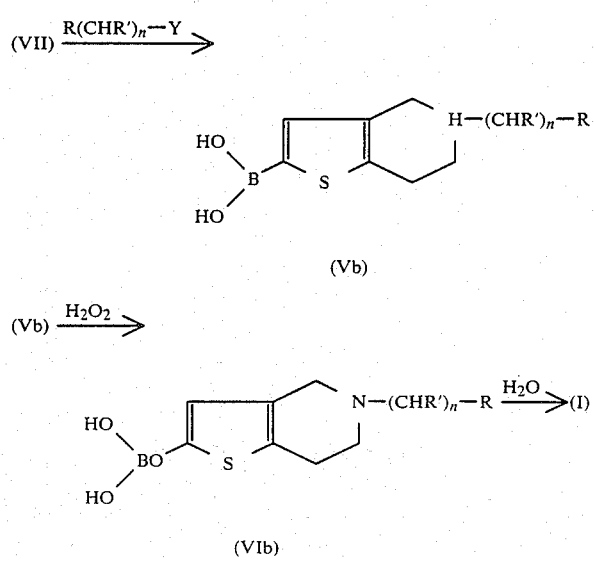

The condensation of the derivative (VII) with the alkylating agent R(CHR')$_n$—Y takes place in an inert solvent, such as a lower alkanol, tetrahydrofuran, dioxan or dimethylformamide, in the presence of a base, such as sodium carbonate or potassium carbonate, which neutralises the HY acid liberated. It is preferable to carry out the condensation at a temperature of from 50° C. to the boiling point of the mixture.

The oxidation of the boronic acid (Vb) with hydrogen peroxide takes place at a temperature of from 0° to 10° C. in an inert solvent, such as tetrahydrofuran or dioxan.

The compound of general formula (II), in which X is a trimethylsilyl radical, and the compound of the formula (VII), which are used as intermediates in the process of the present invention, are novel compounds.

The compound of the formula (II), in which X is a trimethylsilyl radical, is prepared by condensing chlorotrimethylsilane with 4,5,6,7-tetrahydro-thieno-[3,2-c]pyridine in the presence of an organic base as an acid acceptor and in an inert solvent. This condensation reaction is preferably carried out at an elevated temperature.

The following Examples are given for the purpose of illustrating the present invention:

EXAMPLE 1

5-(o-Chlorobenzyl)-5,6,7,7a-tetrahydro-4H-thieno-[3,2-c]pyridin-2-one; formula (I), R=2-Cl-$C_6H_4$; R'=H; n=1; derivative No. 1

79 cc. of a 12% solution of butyl lithium in hexane (0.147 mol) are added dropwise to a solution, cooled to −20° C., of 32.6 g. (0.123 mol) 5-(o-chlorobenzyl)-4,5,6,7-tetrahydrothieno[3,2-c]pyridine in 320 cc. tetrahydrofuran (THF). At the end of the addition, the lithium derivative (III) precipitates and the temperature is allowed to return to 0° C. 15 cc. Hexamethylphosphotriamide (HMPT), previously dried over a 4 Å molecular sieve, are then added. The precipitate becomes dark red.

The temperature is lowered to −40° C. and a solution of 39.8 cc. (0.147 mol) tributyl borate in 40 cc. anhydrous tetrahydrofuran is added dropwise in the course of half an hour. The precipitate disappears and the reaction mixture becomes light yellow. The temperature is kept at −40° C. for half an hour and then returned to 10° C. for 2 hours. 33 cc. (0.291 mol) 30% hydrogen peroxide are added dropwise, whilst keeping the temperature of the reaction mixture below 30° C., an intense precipitate forming during the addition. Stirring is continued for 1 hour at ambient temperature. The reaction mixture is then poured into water and extracted with 3×200 cc. diethyl ether and the organic phases are dried over anhydrous sodium sulphate and concentrated in vacuo at a temperature below 40° C. The remaining liquid is chromatographed over a silica column (using a 6/4 v/v cyclohexane/ethyl acetate mixture) to remove residual HMPT. After evaporation of the solution obtained, the residue is treated with a molar equivalent of oxalic acid in acetone, the light yellow crystals formed being filtered off.

Upon recrystallisation from ethanol, beige crystals of the oxalate are obtained; yield 52% of theory; m.p. 170° C.; IR(KBr): $\nu_{CO}$: 1660 cm$^{-1}$ (broad).

Base: m.p. 73°–74.5° C. (recrystallised from ethanol); NMR (CDCl$_3$): 7.1–7.6 (m,4H); 6.2 (s,1H); 4.2–4.7 (m,1H); 3.9 (s,2H); 1.5–4.2 (m,6H).

Hydrochloride hemihydrate: m.p. decomposes at about 180° C. (precipitated from acetone).

EXAMPLE 2

5-Benzyl-5,6,7,7a-tetrahydro-4H-thieno[3,2-c]-pyridin-2-one; formula (I); R=$C_6H_5$; R'=H; n=1; derivative No. 2

This is prepared in accordance with the procedure of Example 1, starting from 5-benzyl-4,5,6,7-tetrahydrothieno[3,2-c]pyridine.

Maleate: beige crystals; m.p. 132°–134° C. (after recrystallisation from isopropanol); yield 33% of theory; IR (KBr): $\nu_{CO}$: 1680 cm$^{-1}$.

Base: NMR (CDCl$_3$): 7.25 (m,5H); 5.90 (s,1H); 3.60 (s,2H).

EXAMPLE 3

5-(p-Chlorobenzyl)-5,6,7,7a-tetrahydro-4H-thieno-[3,2-c]pyridin-2-one; formula (I): R=4-Cl-$C_6H_4$; R'=H; n=1; derivative No. 3

This is prepared in accordance with the procedure of Example 1, starting from 5-(p-chlorobenzyl)-4,5,6,7-tetrahydrothieno[3,2-c]pyridine.

Maleate: Beige crystals; m.p. 158°–160° C. (recrystallised from ethanol); yield 42% of theory; IR (KBr): $\nu_{CO}$=1680 cm$^{-1}$.

Base: NMR (CDCl$_3$): 7.30 (m,4H); 6.0 (s,1H); 3.50 (s,2H).

EXAMPLE 4

5-(o-Methylbenzyl)-5,6,7,7a-tetrahydro-4H-thieno-[3,2-c]pyridin-2-one; formula (I), R=2-CH$_3$-$C_6H_4$-; R'=H; n=1; derivative No. 4

This is prepared in accordance with the procedure of Example 1, starting from 5-(o-methylbenzyl)-4,5,6,7-tetrahydrothieno[3,2-c]pyridine.

Oxalate: Beige crystals; m.p. 195°–197° C. (recrystallised from methanol); yield 33% of theory; IR (KBr): $\nu_{CO}$=1690 cm$^{-1}$.

Base: NMR (CDCl$_3$): 7.10 (s,4H); 5.90 (s,1H); 3.55 (s,2H); 2.30 (s,3H).

EXAMPLE 5

5-[1-(2-Chlorophenyl)-ethyl]-5,6,7,7a-tetrahydro-4H-thieno[3,2-c]pyridin-2-one; formula (I); R=2-Cl-$C_6H_4$; R'=CH$_3$; n=1; derivative No. 5

This is prepared in accordance with the procedure of Example 1, starting from 5-[1-(2-chlorophenyl)-ethyl]-4,5,6,7-tetrahydrothieno[3,2-c]pyridine.

Hydrochloride: yellow crystals; m.p. 140°–142° C.; yield 24% of theory; IR (KBr): $\nu_{CO}$=1690 cm$^{-1}$.

Base: NMR (CDCl$_3$): 7.30 (m,4H); 6.05 and 5.95 (2s,1H) (2 diastereoisomers).

EXAMPLE 6

5-[1-(2-Chlorophenyl)-propyl]-5,6,7,7a-tetrahydro-4H-thieno[3,2-c]pyridin-2-one; formula (I); R=2-Cl-$C_6H_4$; R'=$C_2H_5$; n=1; derivative No. 6

This is prepared in accordance with the procedure of Example 1, starting from 5-[1-(2-chlorophenyl)-propyl]-4,5,6,7-tetrahydrothieno[3,2-c]pyridine.

Hydrochloride: beige crystals; m.p. 124°–126° C.; yield 27% of theory; IR (KBr): $\nu_{CO}$=1690 cm$^{-1}$.

Base: NMR (CDCl$_3$): 7.30 (m,4H); 6.05 and 5.90 (2s,1H) (2 diastereoisomers).

EXAMPLE 7

5-Trimethylsilyl-4,5,6,7-tetrahydro-thieno[3,2-c]-pyridine; formula (II); X=(CH$_3$)$_3$Si.

65 g. (0.628 mol) Chlorotrimethylsilane in 50 cc. toluene are added, under an atmosphere of nitrogen, to a solution of 80 g. (0.571 mol) 4,5,6,7-tetrahydrothieno[3,2-c]pyridine and 63.4 g. (0.28 mol) triethylamine in 1100 cc. toluene. The reaction mixture is heated to 80° C. for 3 hours. After cooling, the white precipitate of triethylamine hydrochloride obtained is filtered off and the filtrate is concentrated in vacuo. The residue is distilled at 60°–70° C./0.1 mm.Hg, to give the desired product in the form of a colourless liquid; yield 55% of theory.

EXAMPLE 8

4,5,6,7-Tetrahydro-thieno[3,2-c]pyridine-2-boronic acid; formula (VII)

45.4 cc. of a 12% solution of butyl lithium in hexane (0.084 mol) are added dropwise, under an atmosphere of nitrogen, to a solution, cooled to −20° C., of 15 g. (0.07 mol) 5-trimethylsilyl-4,5,6,7-tetrahydrothieno[3,2-c]pyridine, prepared as in Example 7, in 150 cc. of THF.

The reaction mixture is allowed to return to 0° C. and 3 cc. HMPT are added thereto. After cooling this mixture to −50° C., a solution of 19.3 g. (0.084 mol) tributyl borate in 30 cc. THF is added dropwise. Stirring is continued for 2 hours, whilst allowing the mixture to return to ambient temperature. 28 cc. 3N hydrochloric acid (0.084 mol) are then added and the precipitate formed is filtered off. The crystals are washed with acetone and with diisopropyl ether and then dried in vacuo. Off white crystals are obtained in quantitative yield; m.p.>260° C.; NMR (D$_2$O): 6.75 (s,1H); 4.10 (m,2H); 2.80–3.50 (m,4H).

EXAMPLE 9

5-(o-Cyanobenzyl)-4,5,6,7-tetrahydro-theno[3,2-c]-pyridine-2-boronic acid; formula (Vb); R=2-CN-C$_6$H$_4$; R′=H; n=1

A mixture of 3.68 g. (0.02 mol) 4,5,6,7-tetrahydro-thieno[3,2-c]pyridine-2-boronic acid, prepared as in Example 8, 9.09 g. (0.06 mol) o-cyanobenzyl chloride and 5.52 g. (0.04 mol) potassium carbonate in 40 cc. dimethylformamide is heated at 80° C. for 3 hours. After evaporating off the solvent, water is added to the reaction mixture, followed by extraction with 3×100 cc. methylene chloride. The organic solution is dried over anhydrous sodium sulphate and then evaporated in vacuo. The crystals obtained are washed with diisopropyl ether. The desired product is obtained in the form of off white crystals; m.p. 140°–142° C.; yield 45% of theory; IR (KBr): $\nu_{CN}$=2220 cm$^{-1}$;

NMR (DMSO, D$_6$): 7.60 (m,4H); 7.25 (s,1H); 3.80 (s,2H); 3.50 (s,2H); 2.80 (s,4H).

EXAMPLE 10

5-(o-Cyanobenzyl)-5,6,7,7a-tetrahydro-4H-thieno[3,2-c]-pyridin-2-one; formula (I); R=2-CN-C$_6$H$_4$; R′=H; n=1; derivative No. 7

0.23 g. (0.006 mol) of 30% hydrogen peroxide solution is added dropwise to a solution, cooled to 5° C., of 1.8 g. (0.006 mol) 5-(o-cyanobenzyl)-4,5,6,7-tetrahydro-thieno[3,2-c]pyridine-2-boronic acid, prepared as in Example 9, in 30 cc. tetrahydrofuran. The reaction mixture is returned to ambient temperature and stirring is continued for 2 hours. Water is added and the reaction mixture is then extracted with methylene chloride. The organic phase is dried over anhydrous sodium sulphate and then concentrated in vacuo. The residue is chromatographed over a silica column (using a 1/1 v/v cyclohexane/ethyl acetate mixture). After evaporating the solution obtained, the residue is treated with one molar equivalent of oxalic acid in acetone and the crystals formed are filtered off. Oxalate: beige crystals; m.p. 176°–178° C. (after recrystallisation from acetonitrile); yield 28% of theory;

IR (KBr): $\nu_{CO}$: 1700 cm$^{-1}$; $\nu_{CN}$: 2210 cm$^{-1}$.

Base: NMR (CDCl$_3$): 7.50 (m,4H); 6.00 (s,1H); 3.80 (s,2H).

EXAMPLE 11

5-(o-Nitrobenzyl)-5,6,7,7a-tetrahydro-4H-thieno[3,2-c]-pyridin-2-one: formula (I); R=2-NO$_2$-C$_6$H$_4$; R′=H; n=1; derivative No. 8

(a) Preparation of 5-(o-nitrobenzyl)-4,5,6,7-tetrahydrothieno[3,2-c]pyridine-2-boronic acid; formula (Vb); R=2-NO$_2$-C$_6$H$_4$; R′=H; n=1

This is prepared in accordance with the procedure of Example 9, starting from 4,5,6,7-tetrahydrothieno-[3,2-c]pyridine-2-boronic acid and o-nitrobenzyl chloride. Brown crystals; m.p. 132°–134° C.; yield 40% of theory;

NMR (DMSO, D$_6$): 8.0 (m,4H); 7.50 (s,1H); 4.00 (s,2H); 3.60 (s,2H); 2.70 (m,4H).

(b) Preparation of derivative No. 8

This is prepared in accordance with the procedure of Example 10, starting from 5-(o-nitrobenzyl)-4,5,6,7-tetrahydrothieno[3,2-c]pyridine-2-boronic acid, prepared as above. Oxalate: beige crystals; m.p. 186°–188° C. (after recrystallisation from isopropanol-ethanol); yield 17% of theory; IR: $\nu_{CO}$=1685 cm$^{-1}$.

Base: NMR (CDCl$_3$): 7.50 (m,4H); 5.95 (s,1H); 3.90 (s,2H).

EXAMPLE 12

5-(o-Bromobenzyl)-5,6,7,7a-tetrahydro-4H-thieno[3,2-c]-pyridin-2-one; formula (I); R=2-Br-C$_6$H$_4$; R′=H; n=1; derivative No. 9.

(a) Preparation of 5-(o-bromobenzyl)-4,5,6,7-tetrahydrothieno[3,2-c]pyridine-2-boronic acid; formula (Vb); R=2-Br-C$_6$H$_4$; R′=H; n=1

This is prepared in accordance with the procedure of Example 9, starting from 4,5,6,7-tetrahydrothieno-[3,2-c]pyridine-2-boronic acid and o-bromobenzyl bromide. Yellow crystals; m.p. 129°–131° C.; yield 53% of theory;

NMR (DMSO, D$_6$): 7.50 (m,5H); 3.70 (m,2H); 3.10 (s,2H); 2.80 (m,4H).

(b) Preparation of derivative No. 9

This is prepared in accordance with the procedure of Example 10, starting from 5-(o-bromobenzyl)-4,5,6,7-tetrahydrothieno[3,2-c]pyridine-2-boronic acid, prepared as above.

Oxalate: beige crystals; m.p. 151°–153° C. (after recrystallisation from isopropanol); yield 5% of theory; IR (KBr): $\nu_{CO}$=1690 cm$^{-1}$.

Base: NMR (CDCl$_3$): 7.30 (m, 4H); 5.95 (s, 1H); 3.75 (s,2H).

The results of the toxicological and pharmacological tests reported below demonstrate the valuable toxicological and pharmacological properties of the compounds of the present invention. These studies were carried out in comparison with the compounds which are most representative of the two French Patent Specifications mentioned above. i.e. 5-(2-chlorobenzyl)-4,5,6,7-tetrahydrothieno[3,2-c]pyridine, hereafter referred to as reference compound A (compound No. 1 of French Patent Specification No. 73 03 503) and 5-(2-cyanobenzyl)-4,5,6,7-tetrahydrothieno[3,2-c]pyridine, hereafter referred to as reference compound B (compound No. 8 of French Patent Specification No. 75 24 486).

The present invention also provides pharmaceutical compositions which, in particular, possesses antiplatelet aggregation and anti-thrombosis properties, which contain at least one compound of general formula (I) and/or an addition salt thereof with a pharmaceutically acceptable inorganic or organic acid, in admixture with a solid or liquid pharmaceutical diluent or carrier.

TOXICOLOGICAL STUDY

This study was concerned with the acute, chronic, sub-chronic and delayed toxicities. The tests, carried out on different species of animals, namely, mice, rats and rabbits, demonstrate the low toxicity of the compounds of the present invention, as well as their good compatibility.

By way of example, the LD 50/24 hours/kg of body weight, calculated according to the method of Miller and Tainter, for intravenous administration to mice is given in Table I below, which lists the results obtained with derivatives according to the present invention and those obtained with reference compounds A and B. These results show that the derivatives of general formula (I) have a toxicity which is lower by at least a factor of two than that of the reference compounds A and B.

TABLE I

| Compounds | LD 50 |
| --- | --- |
| No. 1 | 113 mg. |
| No. 2 | 116 mg. |
| No. 3 | 125 mg. |
| No. 4 | 110 mg. |
| No. 5 | 286 mg. |
| No. 6 | 121 mg. |
| No. 7 | 254 mg. |
| No. 8 | 278 mg. |
| No. 9 | 118 mg. |
| reference compound A | 55 mg. |
| reference compound B | 45 mg. |

The tests also show that the compounds according to the present invention did not cause any local or general reaction, any disturbance in the biological controls normally carried out or any microscopic or macroscopic lesions in the animals of the various tested species, throughout the various tests carried out.

A study of the subsequent generations did not show any teratogenic effect.

PHARMACOLOGICAL STUDY

This was concerned with the inhibiting action on platelet aggregation and with anti-thrombosis activity, in comparison with reference compounds A and B.

(1) Inhibiting action on platelet aggregation

A sample of blood is taken from the jugular vein of Wistar rats, which have previously been treated with the compound to be tested. From this blood, which is citrate-treated and centrifuged, there is reconstituted a plasma containing 600,000±20,000 platelets per mm$^3$, which is employed in all the aggregation measurements.

(a) Measurement of the platelet aggregaton by ADP 0.4 ml. of plasma is treated in a siliconised tube provided with a bar magnet which is also siliconised. The tube is introduced into an aggregometer connected to an apparatus with which variations in optical density can be recorded. When the light transmission has reached a stable value, 0.5 ml. of a solution containing 10M of ADP (adenosine diphosphate) is introduced into the tube.

Platelet aggregation then causes an increase in light transmission, followed by a reduction in light transmission due to the subsequent disaggregation stage.

The maximum variation in optical density thus determined relative to that of a plasma free of platelets characterises the intensity of aggregation.

The measurements are carried out during the 2 hours which follow the taking of the blood sample, this sample being taken 3 hours after treatment with the derivative to be tested.

(b) Measurement of the platelet aggregation by collagen

The ADP solution is replaced by a solution of collagen (extracted from cattle tendons).

(c) Results

Groups of 20 rats were used. Each group received a single dose of the compound to be tested, administered orally, the same compound being administered at different doses ranging from 5 mg./kg. to 100 mg./kg.

The significant activity of the compounds of general formula (I) manifests itself at a dose of 12.5 mg./kg., whereas in the case of reference compounds A and B, it is necessary to use doses of 100 mg./kg. to achieve a similar activity.

The results obtained are given in the following Tables II and III, which show the percentage inhibition of platelet aggregation obtained relative to the control experiment, 3 hours after treatment with the compound to be tested.

TABLE II

| | ADP TEST | | | | |
| --- | --- | --- | --- | --- | --- |
| | Percentage inhibition | | | | |
| | 5 mg/kg | 12.5 mg/kg | 25 mg/kg | 50 mg/kg | 100 mg/kg |
| Derivative 1 | 51.0 | 83.6 | 83.7 | 84.0 | 84.1 |
| Derivative 2 | 47.8 | 82.6 | 82.9 | 83.7 | 83.7 |
| Derivative 3 | 48.1 | 82.4 | 83.0 | 83.5 | 83.6 |
| Derivative 4 | 48.0 | 81.9 | 82.1 | 82.8 | 82.9 |
| Derivative 5 | 48.4 | 82.0 | 82.4 | 83.2 | 83.5 |
| Derivative 6 | 48.7 | 83.0 | 83.4 | 83.9 | 83.9 |
| Derivative 7 | 47.6 | 82.7 | 82.9 | 83.1 | 83.2 |
| Derivative 8 | 48.0 | 82.8 | 83.1 | 83.3 | 83.4 |
| Derivative 9 | 48.4 | 83.1 | 83.4 | 83.7 | 84.0 |
| Reference compound A | 0 | 0 | 0 | 34.6 | 63.2 |
| Reference compound B | 0 | 0 | 0 | 35.5 | 63.8 |

TABLE III

| | COLLAGEN TEST | | | | |
| --- | --- | --- | --- | --- | --- |
| | Percentage inhibition | | | | |
| | 5 mg/kg | 12.5 mg/kg | 25 mg/kg | 50 mg/kg | 100 mg/kg |
| Derivative 1 | 16.8 | 46.8 | 86.7 | 89.6 | 89.8 |
| Derivative 2 | 16.5 | 44.2 | 85.8 | 87.0 | 87.8 |
| Derivative 3 | 17.4 | 44.9 | 86.5 | 87.2 | 88.1 |
| Derivative 4 | 17.1 | 45.2 | 85.9 | 88.1 | 88.2 |
| Derivative 5 | 17.0 | 44.8 | 86.1 | 87.8 | 88.0 |
| Derivative 6 | 16.8 | 44.4 | 85.7 | 89.0 | 89.2 |
| Derivative 7 | 16.5 | 44.5 | 86.2 | 87.9 | 89.4 |
| Derivative 8 | 17.0 | 44.6 | 86.2 | 88.2 | 88.7 |
| Derivative 9 | 17.2 | 44.9 | 86.4 | 87.6 | 88.6 |
| Reference compound A | 0 | 0 | 40.9 | 46.8 | 80.1 |
| Reference compound B | 0 | 0 | 38.5 | 51.2 | 78.8 |

(d) Kinetic study of platelet aggregation

A further experiment was carried out, relating to the kinetic study of the compounds of the present invention. Derivative No. 1 and reference compound A are dissolved in propylene glycol and administered intraperitoneally to rats at a dose of 100 mg./kg. of body weight, whereas control mice were only given 1 ml./kg. of propylene glycol, again intraperitoneally.

The blood sample is taken 10 minutes and 60 minutes after this administration and is centrifuged to obtain a plasma enriched in platelets.

The platelet aggregation in the plasma, induced by ADP is measured in a Bryston aggregometer, using Born's nephelometric method.

The percentage inhibition as a function of time, obtained by these experiments, is given in the following Table IV:

TABLE IV

| Time in minutes | Derivative according to the present invention, No. 1 | Reference compound A | Control (propylene) glycol |
| --- | --- | --- | --- |
| 10 | 42 | 22 | 0 |
| 60 | 97 | 39 | 0 |

This Table shows that the derivative according to the present invention has a platelet aggregation-inhibiting activity which is much greater than that of reference compound A and that this activity also manifests itself more rapidly; this experiment confirms the results described hereinbefore.

(2) Anti-thrombosis activity

This activity was studied by the experimental thrombosis method caused by extracorporal circulation, described by Umetsu and Sonoi (Thrombos. Haemost., 39, 1/1878).

The left jugular vein and the right external carotid are exposed in rats anaesthetised by an intraperitoneal injection of pentobarbital. A shunt is provided which consists of a central catheter and two lateral catheters. A natural white silk thread is introduced into the central part and the circulation is restarted for 20 minutes. After stopping the circulation by clamping, the thread is gently withdrawn and weighed immediately. The average weight of the moist silk thread was previously found to be 5.10 mg.

Treatment was carried out for 48 hours, 24 hours and 2 hours before the start of the blood circulation in shunt.

The test compounds were administered orally to different groups of animals in the form of a suspension in 10 ml. of 5% gum arabic/kg., the doses used being 12.5 mg./kg., 25 mg./kg., 50 mg./kg., 100 mg./kg. and 200 mg./kg.

The following Table V gives the results of the tests carried out with derivatives 1 and 3 of general formula (I) and with reference compound A and represent the mean values calculated for each group of animals.

TABLE V

| Test compounds | Average weight of the thrombi (mg.) | | | | |
| --- | --- | --- | --- | --- | --- |
| | 12.5 mg/kg | 25 mg/kg | 50 mg/kg | 100 mg/kg | 200 mg/kg |
| Derivative No. 1 | 27.45 | 12.21 | 6.01 | 4.76 | — |
| Derivative No. 3 | 26.72 | 12.04 | 5.96 | 4.62 | — |
| Reference compound A | 30.45 | 30.09 | 28.86 | 23.04 | 23.13 |
| Control, 5% strength gum arabic | 30.41 | | | | |

This test clearly shows the activity of the compounds of the present invention, which considerably reduce the average weight of the thrombi from a dose of 25 mg./kg. upwards, whereas reference compound A has no anti-thrombosis action whatsoever, even at high doses.

Furthermore, the tests show that, in contradistinction to the compounds of French Patent Specifications Nos. 73 03 503 and 75 24 486, the compounds of general formula (I) are entirely devoid of anti-inflammatory properties and vasodilatory effects. Hence, they have much more selective properties, which makes them very valuable in the therapeutic field, where certain supplementary activities, when these are not desired, can be detrimental to the patient.

The toxicological and pharmacological studies which have been reported above show the low toxicity of the compounds of the present invention and their good compatibility, as well as their valuable platelet aggregation-inhibiting and anti-thrombosis properties, which make them very useful in human and veterinary therapy.

The pharmaceutical compositions according to the present invention can be administered orally in the form of, for example, tablets, dragee-coated tablets, capsules of drops, parenterally in the form of injectable solutions and rectally in the form of suppositories.

Each unit dose advantageously contains from 0.010 to 0.500 g. of active material and the daily doses which can be administered can vary from 0.010 to 1.50 g. of active material, depending upon the age of the patient and the severity of the condition to be treated.

Some pharmaceutical formulations according to the present invention are given below by way of example:

(1) Dragee-coated tablets

Derivative No. 1: 0.050 g.
Excipients: lactose, microcrystalline cellulose, magnesium stearate, colophany, shellac, gum arabic, talc. edible gelatine, white wax, erythrosin.

(2) Tablets

Derivative No. 3: 0.075 g.
Excipients: microcrystalline cellulose, sucrose, corn starch, magnesium stearate.

(3) Capsules

Derivative No. 4: 0.050 g.
Excipients: wheat starch, talc, lactose.

(4) Injectable solution

Derivative No. 7: 0.100 g.
Excipient: isotonic solvent to make up to 5 ml.

(5) Suppositories

Derivative No. 8: 0.075 g.
Excipient: semi-synthetic triglycerides.

The pharmaceutical compositions according to the present invention may be used with advantage because of their anti-platelet aggregation and anti-thrombosis activities. Because of their properties of inhibiting certain platelet functions, which can become involved in the mechanism of formation of arterial and venous thromboses, the compositions can be used for the treatment and prophylaxis of platelet disturbances in extracorporal circulation systems or subsequent to atheroma complications.

Reference compound A is 5-(2-chlorobenzyl)-4,5,7,7-tetrahydrothiéno (2,3-c)pyridine Reference compound B is 5-(2-cyanobenzyl)-4,5,6,7-tetrahydrothiéno (3,2-c)pyridine

What is claimed is:

1. A process for the preparation of a compound of the formula:

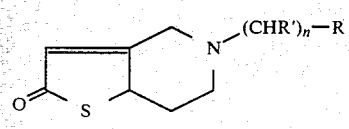 (I)

in which R is hydrogen or phenyl, R' is hydrogen or a lower alkyl and n is 0, 1, 2, 3, or 4, which comprises the steps of:

(a) oxidizing a boronic acid derivative of the formula:

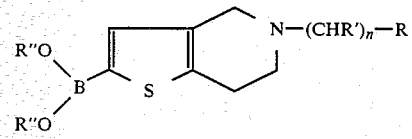 (V)

in which R, R' and n are as hereinbefore described, and R'' is a hydrogen atom or a lower alkyl radical, so as to obtain the boric derivative of the formula;

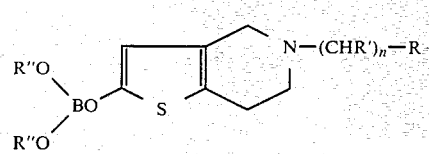 (VI)

in which R, R',R'' and n are as hereinbefore described, and then, (b) hydrolyzing said boric acid derivative to obtain a compound of formula (I).

2. The process according to claim 1, wherein the oxidation is carried out with hydrogen peroxide in an inert solvent under conditions which prevent a rise in temperature of the reaction mixture.

3. The process according to claim 1 wherein the hydrolysis is carried out by contacting the reaction mixture with water.

4. The process according to claim 1 including treating the compound obtained with a mineral or organic acid.

5. The process of claim 1 wherein the compount obtained is 5-(o-chlorobenzyl)-5,6,7,7a-tetrahydro-4H-thieno [3,2-c]pyridin-2-one.

6. The process of claim 1 wherein the compound obtained is 5-benzyl-5,6,7,7a-tetrahydro-4H-thieno[3,2-c]pyridin-2-one.

7. The process of claim 1 wherein the compound obtained is 5-(p-chlorobenzyl)-5,6,-7,7a-tetrahydro-4H-thieno[3,2-c]pyridin-2-one.

8. The process of claim 1 wherein the compound obtained is 5-o-methylbenzyl)-5,-6,7,7a-tetrahydro-4H-thieno [3,2-c]pyridin-2-one.

9. The process of claim 1 wherein the compound obtained is 5-[1-(2-chlorophenyl)-ethyl[-5,6,7,7a-tetrahydro-4-H-thieno]3,2,-c]pyridin-2-one.

10. The process of claim 1 wherein the compound obtained is 5-[1-(2-chlorophenyl)-propyl]-5,6,7,7a-tetrahydro-4H-thieno[3,2-c]pyridin-2-one.

11. The process of claim 1 wherein the compound obtained is 5-(o-cyanobenzyl)-5,6-7,7a-tetrahydro-4H-thieno[3,2-c]pyridin-2-one.

12. The process of claim 1 wherein the compound obtained is 5-(o-nitrobenzyl)-5,6,-7,7a-tetrahydro-4H-thieno[3,2-c]pyridin-2-one.

13. The process of claim 1 wherein the compound obtained is 5-o-bromobenzyl)-5,6,-7,7a-tetrahydro-4H-thieno[3,2-c]pyridin-2-one.

* * * * *